United States Patent [19]

Neiland et al.

[11] 3,935,239

[45] Jan. 27, 1976

[54] PROCESS FOR PRODUCING AROMATIC α-DIKETONES

[76] Inventors: Oyar Yanovich Neiland, ulitsa Raunaya, 45 korpus 3, kv. 127; Yana Nikolaevna Kreitsberga, ulitsa Gorkogo 18, kv. 3, both of Riga, U.S.S.R.

[22] Filed: Mar. 15, 1974

[21] Appl. No.: 451,597

Related U.S. Application Data

[63] Continuation of Ser. No. 252,464, May 11, 1972, abandoned.

[52] U.S. Cl................................. 260/469; 260/590
[51] Int. Cl.².................... C07C 69/76; C07C 49/76
[58] Field of Search............................ 260/590, 469

[56] References Cited
UNITED STATES PATENTS 3,321,525   5/1967   Griesbaum et al.................. 260/590

OTHER PUBLICATIONS

Re et al., Chem. Abstracts 72, 42809n (1970).

*Primary Examiner*—D. Horwitz
*Attorney, Agent, or Firm*—Haseltine, Lake & Waters

[57]        ABSTRACT

A process for producing α-diketones which comprises oxidizing diaryl-substituted acetylenes with potassium permanganate in an aqueous acetone solution preferably in the presence of acetic acid.

4 Claims, No Drawings

PROCESS FOR PRODUCING AROMATIC α-DIKETONES

This application is a continuation of Ser. No. 252,464 filed May 11, 1972, now abandoned.

The present invention relates to the production of aromatic alpha-diketones used as monomers for the synthesis of heat-resistant polymers.

Two processes are known for producing aromatic alpha-diketones such as bis-p-(phenyl-glyoxalyl)benzene.

In the first process the starting material used is critical p-diacetylbenzene which is transformed into p-bis(-carboxymethyl)benzene by way of a two-stage synthesis. The next stage involves the production of p-bis(carboxymethyl)benzene chloride which is used for the acylation of benzene. The resulting p-bis($\omega$-phenacyl)-benzene is oxidized into the desired product by selenium dioxide. Therefore, the synthesis comprises at least five stages; the duration of the entire process is 55 hours, and the yield of the desired product is only 29.8% based on the starting p-diacetylbenzene.

In the second process the starting material used is dicyanobenzene which is transformed into p-bis(-phenylacetyl)benzene by way of magnesium-organic synthesis. Said p-bis(phenylacetyl)benzene is then subjected to condensation with p-nitrosodimethylaniline and the resulting condensation product is hydrolyzed to give the desired product. The synthesis comprises at least three stages; the entire process duration is 44 hours and the yield is 10.9% based on the starting dicyanobenzene. M.Ogliarusso, E.Beck J.Org.Chem., 30, 3354 (1965).

It is an object of the present invention to provide a novel process for the production of aromatic alpha-diketones with an increased yeild.

It is another object of the present invention to provide a novel process for the production of aromatic alpha-diketones which would eliminate the use of critical starting materials.

Still another object of the present invention is to provide a novel process for the production of aromatic alpha-diketones which would enable reducing the process duration.

A further object of the invention is to provide a novel process for the production of aromatic alpha-diketones which would require no special equipment.

These objects are accomplished by a process for producing aromatic $\alpha$-diketones which, in accordance with the present invention, comprises oxidizing diarylsubstituted acetylenes with potassium permanganate in aqueous acetone.

The oxidation of diaryl-substituted acetylenes with potassium permanganate is conducted in amounts corresponding to the stoichiometric amount.

To enhance the desired product yield, it is advisable to carry out the reaction in the presence of acetic acid. In this case the yield of an aromatic $\alpha$-diketone is increased from 60 to 80–90%.

To accelerate the reaction of oxidizing diaryl-substituted acetylenes, the process is conducted at the solvent boiling temperature, viz. at the boiling point of acetone. Under such conditions the oxidation reaction time is reduced to 40 min.

The starting diaryl-substituted acetylenes may be readily obtained from dihalo-derivatives and copper phenylacetylide.

In practice of the present invention the above-mentioned process may be embodied as follows. In a flask diarylsubstituted acetylene and potassium permanganate are charged in stoichiometric amounts, whereafter a solvent, viz., acetone and water (employed in a volumetric ratio of 5:1 to 8:1 respectively), and acetic acid in a molar ratio to the potassium permanganate of 1:1 are added. The mixture is refluxed with stirring until the complete discoloration of the solution and filtered; the residue is washed with acetone. The filtrate is evaporated, diluted with water; the residue is filtered and crystallized.

As may be seen from the above-given description, the process according to the present invention is simple, as it consists of one stage only, and the duration thereof is not longer than 3 hours; the starting materials are readily available, and the entire process may be conducted using conventional equipment. The product yield is as high as 81 to 90%.

The following specific examples are given for a better understanding and illustration of the present invention,

EXAMPLE 1

PRODUCTION OF BIS-P-(PHENYLGLYOXALYL)BENZENE 0.55 g (0.002M) of 1,4-bis(phenylethynyl)benzene are dissolved in 40 ml of acetone, and 5 ml of water and 0.5 ml (0.008M) of acetic acid are added thereto; then 1.26 g (0.008M) of potassium permanganate are added to the mixture under stirring. The mixture is stirred for 40 minutes upon heating at reflux. The resulting reaction mass is filtered and the residue is washed several times with hot acetone. The filtrate is evaporated to a volume of 10 ml and diluted with 200 ml of water. Recrystallizaion from ethanol gives needle-like yellow crystals. The yield is 0.61 g (89% of the theoretical value m.p. 125–126°C).

EXAMPLE 2

PRODUCTION OF BENZIL

Benzil is produced in a manner similar to that described in Example 1. Reaction of 3.16 g (0.02M) of potassium permanganate with 1.78 g (0.01M) of diphenylacetylene in solution in 25 ml of acetone, 5 ml of water, and 1.26 ml (0.02M) of acetic acid gives a yellow substance in the form of needle-like crystals. The yield is 1.8 g (86%); m.p. 93°–94°C.

EXAMPLE 3

PRODUCTION OF P-NITROBENZIL 0.5 g (0.002M) of p-nitrololane is dissolved in 15 ml of acetone, mixed with 2 ml of water, 0.27 ml (0.004M) of acetic acid and 0.7 g (0.004M) of potassium permanganate under stirring. The mixture is heated at reflux for 15 minutes under stirring. The resulting mass is filtered, and the residue is washed several times with hot acetone. The filtrate is evaporated to a volume of 5 ml and diluted with 100 ml of water. Recrystallization from ethanol gives yellow crystals of p-nitrobenzil. The yield is 0.45 g (79%); m.p. 140°–142°C.

EXAMPLE 4

PRODUCTION P-CARBOMETHOXYBENZIL

This compound is produced in a manner similar to that disclosed in the previous Example 3. Reaction of 0.47 g (0.02M) p-carbomethoxytolane in 15 ml of acetone, 0.7 g (0.004M) of potassium permanganate, 3 ml of water, and 0.27 ml (0.004M) of acetic acid gives a yellow substance in the needle-like form which is p-carbomethoxybenzil. The yield is 0.4 g (75%); m.p. 224°–225°C. Found (%): C: 71.69; H: 4.39; $C_{16}H_{12}O_4$. Calculated (%): C: 71.64; H: 4.47. IR-spectrum ($cm^{-1}$): 1,680 (38); 1,670 (44); 1,599 (15); 1,574 (10); 1,508. (10).

We claim:

1. A process for producing aromatic α-diketones, which comprises oxidizing 1,2-diphenylacetylene compounds with potassium permanganate in an aqueous acetone solution at a volumetric ratio of acetone to water of from 5:1 to 8:1 and at the boiling point of the reaction mixture.

2. A process as claimed in claim 1, wherein the oxidation is effected in the presence of acetic acid at a molar ratio of acetic acid to potassium permanganate of 1:1.

3. A process as claimed in claim 1, wherein the oxidation is effected using a stoichiometric amount of potassium permanganate.

4. A process as claimed in claim 3 wherein the 1,2-diphenylacetylene compounds are selected from the group consisting of 1,2-diphenylacetylene, nitro and carbomethoxy derivatives thereof and bis (phenyethynyl benzene.

\* \* \* \* \*